(12) United States Patent
Huang et al.

(10) Patent No.: US 11,752,082 B2
(45) Date of Patent: Sep. 12, 2023

(54) COSMETIC COMPOSITION FOR THE OXIDATIVE DYEING OF KERATIN FIBRES

(71) Applicant: L'OREAL, Paris (FR)

(72) Inventors: Ping Huang, Shanghai (CN); Wei Wei, Shanghai (CN); Philippe Rapold, Shanghai (CN)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/623,074

(22) PCT Filed: Jun. 28, 2019

(86) PCT No.: PCT/CN2019/093593
§ 371 (c)(1),
(2) Date: Dec. 27, 2021

(87) PCT Pub. No.: WO2020/258220
PCT Pub. Date: Dec. 30, 2020

(65) Prior Publication Data
US 2022/0313577 A1  Oct. 6, 2022

(51) Int. Cl.
| *A61Q 5/10* | (2006.01) |
| *A61K 8/49* | (2006.01) |
| *A61K 8/22* | (2006.01) |
| *A61K 8/34* | (2006.01) |
| *A61K 8/41* | (2006.01) |
| *A61K 8/46* | (2006.01) |
| *A61K 8/23* | (2006.01) |
| *A61K 8/44* | (2006.01) |
| *A61K 8/67* | (2006.01) |
| *A61K 8/81* | (2006.01) |
| *A61K 8/04* | (2006.01) |

(52) U.S. Cl.
CPC ............. *A61K 8/494* (2013.01); *A61K 8/046* (2013.01); *A61K 8/22* (2013.01); *A61K 8/23* (2013.01); *A61K 8/347* (2013.01); *A61K 8/411* (2013.01); *A61K 8/415* (2013.01); *A61K 8/447* (2013.01); *A61K 8/46* (2013.01); *A61K 8/4926* (2013.01); *A61K 8/4953* (2013.01); *A61K 8/676* (2013.01); *A61K 8/8147* (2013.01); *A61K 8/8158* (2013.01); *A61Q 5/10* (2013.01); *A61K 2800/4324* (2013.01); *A61K 2800/48* (2013.01); *A61K 2800/522* (2013.01); *A61K 2800/5424* (2013.01); *A61K 2800/882* (2013.01)

(58) Field of Classification Search
CPC .......... A61K 8/494; A61K 8/046; A61K 8/22; A61K 8/23; A61K 8/347; A61K 8/411; A61K 8/415; A61K 8/447; A61K 8/46; A61K 8/4926; A61K 8/4953; A61K 8/676; A61K 8/8147; A61K 8/8158; A61K 2800/4324; A61K 2800/48; A61K 2800/522; A61K 2800/5424; A61K 2800/882; A61Q 5/10
USPC ...................................................... 8/406, 405
See application file for complete search history.

(56) References Cited

U.S. PATENT DOCUMENTS

| 3,413,072 A | 11/1968 | Ghilardi et al. |
| 5,520,706 A | 5/1996 | Samain et al. |
| 2003/0028977 A1* | 2/2003 | Lang ............... A61K 8/411 8/405 |
| 2003/0226217 A1 | 12/2003 | Bowes et al. |
| 2004/0143912 A1 | 7/2004 | Legrand et al. |
| 2006/0078522 A1 | 4/2006 | Vic |
| 2014/0223670 A1* | 8/2014 | Wagner ............. A61K 8/022 8/406 |
| 2015/0328128 A1* | 11/2015 | Hao ................. A61K 8/86 206/581 |
| 2016/0159552 A1* | 6/2016 | Neuba ............... A61Q 5/08 8/406 |
| 2017/0165171 A1 | 6/2017 | Knappe et al. |

FOREIGN PATENT DOCUMENTS

| BR | 112021025534 A2 | 3/2022 |
| CN | 1602836 A | 4/2005 |
| CN | 101980750 A | 2/2011 |
| CN | 103781465 A | 5/2014 |
| CN | 105828882 A | 8/2016 |
| CN | 109718124 A | 5/2019 |
| EP | 1 314 418 A1 | 5/2003 |
| EP | 2 422 762 A1 | 2/2012 |
| FR | 2 848 109 A1 | 6/2004 |
| JP | 2013-112641 A | 6/2013 |
| WO | WO 2006/060568 A1 | 6/2006 |
| WO | WO 2009/010883 A2 | 1/2009 |
| WO | WO 2012/076538 A1 | 6/2012 |
| WO | WO 2014/202150 A1 | 12/2014 |
| WO | WO 2015/097099 A1 | 7/2015 |

OTHER PUBLICATIONS

International Search Report dated Mar. 25, 2020 in PCT/CN2019/093593, filed Jun. 28, 2019, 4 pages.
Office Action dated Jun. 12, 2023 to Chinese Patent Application No. 201980097948.4, (with Google English Translation), 32 pages.
Office Action dated Mar. 29, 2023 to Brazilian Patent Application No. BR112021025534, (with Google English Translation), 8 pages.
Zviak Charles, "Science des traitement capillaires", Sciencedes Traitements Capillaires, (1988), pp. 271-273.

* cited by examiner

*Primary Examiner* — Eisa B Elhilo
(74) *Attorney, Agent, or Firm* — Oblon, McClelland, Maier & Neustadt, L.L.P.

(57) ABSTRACT

A dye composition I, comprises: a) at least one oxidative dye(s), b) at least one thickener selected from anionic polymer(s), and c) at least one antioxidant including thiol-derived reducer(s). A kit comprises (1) the dye composition I and (2) oxidizing composition IL, comprising at least one oxidant.

20 Claims, No Drawings

COSMETIC COMPOSITION FOR THE OXIDATIVE DYEING OF KERATIN FIBRES

TECHNICAL FIELD

The present invention relates to a cosmetic composition for the oxidative dyeing of keratin fibres, in particular human keratin fibres such as the hair.

BACKGROUND

Many people have for a long time sought to modify the colour of their hair, and especially to dye it in order, for example, to mask their grey hair. "Permanent" dyeing methods also known as oxidative dyeing, which use dye compositions containing oxidative dye precursors, generally referred to as oxidation bases, such as ortho- or para-phenylenediamines, ortho- or para-aminophenols and heterocyclic compounds, have been developed for dyeing human keratin fibres in a long-lasting manner. These oxidation bases are colourless or weakly coloured compounds, which, when combined with oxidizing products, may give rise to coloured compounds via a process of oxidative condensation.

The dyeing product can comprise both at least one oxidative dye and at least one oxidant. For better use, the oxidative dye and the oxidant may be placed respectively in a multi-compartment package, and are mixed together immediately before use. Plastics (PA, PP. PCTA etc.) have been developed to form the package. However, plastic is generally much less favorable than conventional aluminum in terms of compatibility with the dye.

SUMMARY OF THE INVENTION

The Applicant has now discovered that the use of a specific antioxidant together with an oxidative dye makes it possible to obtain a cosmetic composition for the oxidative dyeing of keratin fibres, which can overcome the above drawbacks and which has further improved properties, in particular improved compatibility with the plastic package.

One subject of the present invention is thus a dye kit for the oxidative dyeing of keratin fibres comprising:
(1) a dye composition I, comprising:
a) at least one oxidative dye(s),
b) at least one anionic polymer(s), and
c) at least one reducer(s); and
(2) an oxidizing composition II, comprising:
d) at least one oxidant.

The present invention also relates to a process for dyeing keratin fibres, in particular human keratin fibres such as the hair, using the dye composition I according to the invention.

At last, the present invention relates to a kit for the oxidative dyeing of keratin fibres, which is suitable for performing the process of the invention.

EMBODIMENTS OF THE INVENTION

The dye kit of the invention is intended to be used in a process for dyeing keratin fibres.

A subject of the invention is thus also a process for dyeing keratin fibres, which consists in mixing the dye composition I with the composition II immediately before use, and applying to the keratin fibres the dye kit of the invention.

Other characteristics and advantages of the invention will emerge more clearly on reading the description and the examples that follow.

Other than in the operating examples, or where otherwise indicated, all numbers expressing quantities of components and/or reaction conditions are to be understood as being modified in all instances by the term "about," meaning within 10% of the indicated number (e.g. "about 10%" means 9%-11% and "about 2%" means 1.8%-2.2%).

Throughout the description, including the claims, the term "comprising a" should be understood as being synonymous with "comprising at least one", unless otherwise mentioned. Moreover, the expression "at least one" used in the present description is equivalent to the expression "one or more".

Throughout the description, including the claims, an embodiment defined with "comprising" or the like should be understood to encompass a preferable embodiment defined with "consisting substantially of" and a preferable embodiment defined with "consisting of".

Preferably, the "keratin material" according to the present invention is the skin. By "skin", we intend all the body skin. Still preferably, the keratin material is the face, or the neck, especially the face.

By a component X "distributed mainly within" a component Y, it meant that when components X and Y are brought into mix, less than 20%, preferably less than 10%, or less than 5%, or less than 1%, or less than 0.5%, of component X is present on surface of component Y.

In the application, unless specifically mentioned otherwise, contents, parts and percentages are expressed on a weight basis.

The terms "oxyalkylenated", "oxyethylenated", "oxypropylenated" and "glycerolated" cover, respectively, mono- or poly-oxyalkylenated, oxyethylenated, oxypropylenated and glycerolated compounds, unless specifically mentioned.

Dye Composition I

The dye composition I of the dye kit according to the present invention can comprise at least one oxidative dye(s), at least one anionic polymer(s), and at least one reducer(s).

Oxidative Dye

As indicated previously, the dye composition I according to the invention comprises one or more oxidative dyes.

The oxidative dyes that may be used in the present invention are generally chosen from oxidation bases, optionally combined with one or more couplers.

Preferentially, the oxidative dye(s) comprise one or more oxidation bases.

The oxidation bases may be chosen especially from para-phenylenediamines, bis(phenyl)alkylenediamines, para-aminophenols, ortho-aminophenols, heterocyclic bases, and the addition salts thereof, and mixtures thereof.

Among the para-phenylenediamines, examples that may be mentioned include para-phenylenediamine, para-tolylenediamine, 2-chloro-para-phenylenediamine, 2-methyl-para-phenylenediamine (CI 76042), 3-methyl-para-phenylenediamine, 4-methyl-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chlo- roaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-paraphenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and the addition salts thereof.

Among the heterocyclic bases, examples that may be mentioned include pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyridine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-Diamino-1-(β-methoxyethyl)pyrazole may also be used.

A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or one of its salts.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or a salt thereof.

The oxidative dye(s) may also comprise one or more couplers, which may be chosen from those conventionally used for the dyeing of keratin fibres.

Among these couplers, mention may be made especially of meta-phenylenediamines, meta-aminophenols, meta-diphenols, naphthalene-based couplers heterocyclic couplers, and also the addition salts thereof, and mixtures thereof.

Examples that may be mentioned include 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy) propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof, such as chlorhydrate or dichlorhydrate thereof, e.g., 1-beta-hydroxyethyloxy-2,4-diamino-benzene dichlorhydrate (2,4-diaminophenoxyethanol hcl).

In general, the addition salts of the oxidation bases and couplers that may be used within the context of the invention are especially chosen from the addition salts with an acid such as the hydrochlorides, hydrobromides, sulfates, citrates, succinates, tartrates, lactates, tosylates, benzenesulfonates, phosphates and acetates.

The oxidation base(s) may advantageously represent from 0.0001% to 10% by weight relative to the total weight of the composition I, preferably from 0.005% to 5% by weight and better still from 0.1% to 5% by weight.

The coupler(s), if they are present, may advantageously represent from 0.0001% to 10% by weight relative to the total weight of the composition I, and preferably from 0.005% to 5% by weight.

Reducer

The inventor has surprisingly discovered that, using a specific reducer, in particular a sulfur-containing reducer, e.g., a thiol-derived reducer, as an antioxidant, the dye composition can be well compatible with a package made of plastic.

According to the present invention, useful reducers can comprise, thiourea sulfite ammonium, thioglycolic acid, thiolactic acid, ammonium thiolactate, mono-carbothioic acid diglycidyl ester, carbothioic ammonium acetate, thioglycerol, dithio glycolic acid, diammonium carbothioic strontium acetate, thio glycolate, carbothioic isooctyl, -DL-cysteine single ethanolamine thio glycolate; cysteine, cysteamine, homocysteine, glutathione peptide, thiomalic acid, 2-mercaptopropionic acid, 3-mercaptopropionic acid, thiodiglycol, 2-mercaptoethanol, dithiothreitol, thioxanthine, thiosalicylic acid thiopropionic acid, lipoic acid, N-acetylcysteine and its salts; ammonium thioglycolate, glycerol monothioglycolate, or a mixture thereof.

Examples of preferred reducers that may be mentioned include thioglycolic acid, dithio glycolic acid, thiolactic acid, thiomalic acid, the salts thereof, or a mixture thereof.

Other Anti-Oxidant

In addition to the reducer introduced above, one or more other anti-oxidant can also be used for the dye composition I according to the present invention.

The antioxidants used may include natural exogenous phytochemical antioxidants such as phenols and carotenoids.

The antioxidant can include flavonoids. Flavonoids constitute a large class of more than 5,000 polyphenolic phytochemicals with antioxidant properties that act by direct free radical scavenging. Flavonoids have anti-inflammatory, antibacterial, antiviral, anti-allergic, anti-mutagenic, anti-thrombotic, anti-tumor and vasodilating effects and these methods of action can also be used to prevent, alleviate or eliminate oxidative damage from dental instruments. Flavonoids also exhibit chelation properties with metal ions and can mitigate oxidative damage from metal ions by chelating ions. The formation and stability of flavonoid-metal chelate is dependent on the function of the structure. Flavonoids having a catechol moiety and having a hydrogen bond between the hydroxyl groups at the 5-position and the 3-position have chelation properties.

Vitamin C and derivatives can be used, including ascorbic acid, sodium ascorbate and the fat-soluble ester tetrahexyl decyl ascorbate and ascorbyl palmitate, magnesium ascorbyl phosphate, ascorbyl glucoside, glucosamine ascorbate, ascorbyl acetate, and the like. In addition, it is also possible to use plants derived from a large amount of vitamin C, such as extracts of Myrciaria *dubia*, acerola, emblica *officinalis*, and bioflavonoids from rose hips and citrus, including Water-soluble bioflavonoids such as hesperidin methyl chalcone.

*Sesamum indicum* or lignan may also be added. Sesame and its lignans (fibrous compounds associated with sesame) act as antioxidants. Sesame seed lignan significantly enhances vitamin E activity.

Other antioxidants which may be incorporated into the compositions of the present invention include tocopherols (e.g., d-alpha-tocopherol, d-beta-tocopherol, d-gamma-tocopherol, d-delta-tocopherol), tocotrienol Phenol (eg d-α-tocotrienol, d-β-tocotrienol, d-γ-tocotrienol, d-δ-tocotrienol) and vitamin E (α-tocopheryl acetate)). These compounds can be isolated from natural sources, prepared by synthetic means or mixed. The tocotrienol-rich vitamin E preparation can be obtained by fractionating the vitamin E preparation to remove a portion of the biophenol and recovering the higher concentrated tocotrienol product. Useful tocotrienols are natural products isolated, for example, from wheat germ oil, grain or palm oil using high performance liquid chromatography or from barley, distiller's grains or oats by alcohol extraction and/or molecular distillation. The term "tocotrienol" as used herein includes a tocotrienol-rich fraction obtained from these natural products as well as a pure compound. Increased glutathione peroxidase activity protects the skin from oxidative damage.

In addition, carotenoids, especially lutein types, are also useful antioxidants that can be used. Lutein-type carotenoids include molecules such as lutein, canthaxantin, cryptoxanthin, zeaxanthin and astaxanthin.

Lutein compounds protect compounds such as vitamin A, vitamin E and other carotenoids.

The flavonoid may be a flavanone (a derivative of 2,3-dihydro-2-phenylbenzopyran-4-one). Flavanones include: scutellarin, eriodictin, hesperetin, hesperidin, *sylvestre*, isosakuranetin, naringenin, naringin, pinocin, tangrin (poncirin)), sakuranetin, sakura glycosides and 7-O-methyl ergophenol (Sterubin).

The flavonoid may be a dihydroflavonol (a derivative of 3-hydroxy-2,3-dihydro-2-phenylbenzopyran-4-one). Flavanols include: taxifolin, Aromadedrin, Chrysandroside A, Chrysandroside B, Xeractinol, astilbin, and flavonol.

The flavonoid may be a flavonoid (a derivative of 2-phenylbenzopyran-4-one). Flavonoids include: Apigenin, luteolin, tangeritin, Chrysin, baicalein, wild baicalein, wogonin, synthetic flavonoids: Diosmin and flavonoids ester.

The flavonoid may be a flavonol (a derivative of 3-hydroxy-2-phenylbenzopyran-4-one). Flavonols include: 3-hydroxyflavone, rhodoxanthin, quercetin, galangin, cotton dermatan, kaempferol, kaempferol, isorhamnetin, mulberry pigment, myricetin, naringin (Natsudaidain), Muskyl flavonol (Pachypodol), quercetin, methyl rhamnosin, rhamnetin, azalein, hyperoside, isoquercetin, kaempferol, myricetin, suede Glycosides, Robinin, Rutin, *Spiraea*, Xanthorhamnin, Amurensin, Icariin and Tracuridine.

The flavonoid may be a flavan-3-ol (a derivative of 2-phenyl-3,4-dihydro-2H-benzopyran-3-ol). Flavan-3-ol includes: catechin, epicatechin, epigallocatechin, epicatechin gallate, epigallocatechin gallate, epiafzelechin, Fisetinidol, Guibourtinidol, Mesquitol and Robinetinidol.

The flavonoid may be a flavan-4-ol (a derivative of 2-phenylchroman-4-ol). Flavan-4-ols include: Apiforol and Luteoforol.

The flavonoid may be an isoflavone (a derivative of 3-phenylbenzopyran-4-one). Isoflavones include: genistein, daidzein, garbanin A, formononetin, and equol metabolites from daidzein.

The antioxidant may be anthocyanin (a derivative of 2-phenylbenzopyranoside cation). Anthocyanins include: Aurantinidin, cyanidin, delphinidin, Europinidin, Luteolinidin, Pelargonidin, Malvidin, Peonyidin (Peonidin)), morning glory pigment (Petunidin), rose pigment (Rosinidin) and xanthone.

The antioxidant may be dihydrochalcone (a derivative of 1,3-diphenyl-1-propanone). Dihydrochalcone includes: phloretin, dihydrochalcone phloridin cisplatin, Aspalathin, naringin dihydrochalcone, neohesperidin dihydrochalcone and Nothofagin. The mode of action of the present invention is not limited, but dihydrochalcone can exert an antioxidant effect by reducing active radicals such as active oxygen and reactive nitrogen species.

The antioxidant can be anthocyanin. Anthocyanins and their derivatives are antioxidants. Anthocyanins comprise a class of flavonoid compounds responsible for the red, purple and blue colors of many fruits, vegetables, grains and flowers, which are naturally occurring water-soluble compounds. In addition, anthocyanins are collagenase inhibitors. Inhibition of collagenase helps prevent and reduce wrinkles caused by skin collagen reduction, increase skin elasticity, and the like. Anthocyanins can be obtained from any part of a variety of plant sources, such as solids, flowers, stems, leaves, roots, bark or seeds. Those skilled in the art will appreciate that certain portions of the plant may contain higher natural levels of anthocyanins, and thus these moieties are used to obtain the desired anthocyanins. In some cases, the antioxidant can include one or more betaine. Betatin, similar to anthocyanins, is available from natural sources and is an antioxidant.

The antioxidant may be a phenylpropanoid (a derivative of cinnamic acid). Phenylpropanoids include: cinnamic acid, caffeic acid, ferulic acid, trans-ferulic acid (including its antioxidant pharmacore 2,6-dihydroxy acetophenome), 5-hydroxyferic acid, sinapic acid, Coumarin, coniferyl alcohol, sinapyl alcohol, eugenol, Chavicol, baicalein, P-coumaric acid and sinapinic acid. Without limiting the mode of action of the present invention, phenylpropanoids can neutralize free radicals.

The antioxidant may be chalcone (a derivative of 1,3-diphenyl-2-propen-1-one). Chalcone includes: zirconia, Okanin, safflower, Marein, Sophoradin, Xanthohumol, Flavokvain A, Flavokavain B, Flavokavin C and Synthetic Safalcone.

The antioxidant may be curcuminoid. Curcuminoids include: curcumin, demethoxycurcumin, bis-demethoxycurcumin, tetrahydrocurcumin, and tetrahydrocurcumin. Curcumin and tetrahydrocurcumin can be derived from the rhizome of turmeric.

Tetrahydrocurcumin, a metabolite of curcumin, has been found to be a more potent antioxidant and more stable than curcumin.

The antioxidant can be tannin. Tannins include: tannins, Terflavin B, Glucogallin, Dgallic acid, and Quercitannic acid.

The antioxidant can be a stilbenoid. The mites include: resveratrol, red sandalwood and paclitaxel. Resveratrol can include, but is not limited to, 3,5,4'-trihydroxyindole, 3,4, 3',5'-tetrahydroxyindole (cetotriol), 2,3',4,5'-Tetrahydroxyindole (oxidized resveratrol), 4,4'-dihydroxyindole and its alpha and beta glucoside, galactoside and mannoside derivatives.

The antioxidant may be coumarin (a derivative of 2H-benzopyran-2-one). Coumarins include: 4-hydroxycoumarin, umbelliferone, Aesculetin, Herniarin, Auraptene, and dicoumarin.

The antioxidant can be a carotenoid. Carotenoids include:
beta-carotene, alpha-carotene, gamma-carotene, beta-cryptoxanthin, lycopene, lutein and idebenone.

The antioxidant can be a vitamin. Vitamins include: retinol, ascorbic acid, L-ascorbic acid, tocopherol, tocotrienol and vitamin cofactor: coenzyme Q10.

The antioxidant may be: xanthone, butylated hydroxytoluene, 2,6-di-tert-butylphenol, 2,4-dimethyl-6-tert-butylphenol, gallic acid, eugenol, uric acid, α-lipoic acid, ellagic acid, cichoric acid, chlorogenic acid, rosmarinic acid, salicylic acid, acetylcysteine, S-allylcysteine, pyridone (Barbigerone), 何 Chebulagic acid, edaravone, ethoxyquin, glutathione, hydroxytyrosol, idebenone, melatonin, N-acetyl serotonin, nordihydroguaiac Acid, Oleotanthal, oleuropein, Paradol, paclitaxel, probucol, propyl gallate, protocatechuic acid, pyrithione, rutin, flax lignan diglucoside, sesamin, sesame phenol, Silybin, silymarin, theaflavins, theaflavins digallate, Thmoquinone, Trolox, tyrosol, polyunsaturated fatty acids and sulfur-based antioxidants such as methionine or lipoic acid.

Vitamin C and derivatives can be used, including ascorbic acid, sodium ascorbate and the fat-soluble ester tetrahexyl decyl ascorbate and ascorbyl palmitate, magnesium ascorbyl phosphate, ascorbyl glucoside, glucosamine ascorbate, ascorbyl acetate, and the like. In addition, it is also possible to use plants derived from a large amount of vitamin C, such as extracts of Myrciaria *dubia*, acerola, emblica *officinalis*, and bioflavonoids from rose hips and citrus, including Water-soluble bioflavonoids such as hesperidin methyl chalcone.

*Sesamum indicum* or sesame lignan can also be used. Sesame and its lignans (fibrous compounds associated with sesame) act as antioxidants. Sesame seed lignan significantly enhances vitamin E activity.

Other antioxidants which may be incorporated into the compositions of the present invention include tocopherols (e.g., d-alpha-tocopherol, d-beta-tocopherol, d-gamma-tocopherol, d-delta-tocopherol), tocotrienol Phenol (eg d-α-tocotrienol, d-β-tocotrienol, d-γ-tocotrienol, d-δ-tocotrienol) and vitamin E (α-tocopheryl acetate)). These compounds can be isolated from natural sources, prepared by synthetic means or mixed. The tocotrienol-rich vitamin E preparation can be obtained by fractionating the vitamin E preparation to remove a portion of the biophenol and recovering the higher concentrated tocotrienol product. Useful tocotrienols are natural products isolated, for example, from wheat germ oil, grain or palm oil using high performance liquid chromatography or from barley, distiller's grains or oats by alcohol extraction and/or molecular distillation. The term "tocotrienol" as used herein includes a tocotrienol-rich fraction obtained from these natural products as well as a pure compound. Increased glutathione peroxidase activity protects the skin from oxidative damage.

In addition, carotenoids, especially lutein types, are also useful antioxidants that can be used. Lutein-type carotenoids include molecules such as lutein, canthaxantin, cryptoxanthin, zeaxanthin and astaxanthin. Lutein compounds protect compounds such as vitamin A, vitamin E and other carotenoids.

The antioxidant, including the reducer, described above is preferably used according to the invention in an amount which may range from 0.001 to 5% by weight, preferably from 0.1 to 3% by weight, more preferably from 0.35 to 2% by weight, relative to the total weight of the dye composition I.

Anionic Polymers

The dye composition I according to the present invention can comprise at least one anionic polymer used as a thickener.

Anionic polymers are water-soluble polymers capable, in an aqueous medium, of reversibly associating together or with other molecules.

Their chemical structure comprises hydrophilic zones and hydrophobic zones characterized by at least one fatty chain.

The anionic polymer of the present invention preferably comes from the copolymerization between 1) and 2):

1) at least one ethylenically unsaturated mono or dicarboxylic acid monomer substituted by at least one, linear or branched, $(C_1-C_{10})$alkyl group; and
2) at least one monomer which is an ester of formula (I):

$$A-O-(Alk-O)_Z-(CH_2)_W-R^a \quad (I)$$

Formula (I) wherein:

A represents a ethylenically unsaturated acyclic residue, optionally containing an additional carboxylic group or it salt, wherein said additional carboxylic group may be esterified with a linear or branched $(C_1-C_{20})$alkyl group;

$R^a$ represents an alkyl a linear or branched $(C_1-C_{30})$alkyl group, alkylaryl or arylalkyl group having from 1 to 30 carbon atoms wherein the alkyl group is linear or branched, preferably $R^a$ represents $(C_1-C_{20})$alkyl group, alkylphenyl or phenylakyl group having from 1 to 20 carbon atoms wherein the alkyl group is linear or branched;

Alk represents a linear or branched $(C_1-C_6)$alkylene group, particularly Alk represents $-CH_2-CH(R^b)-$ wherein $R^b$ represents a hydrogen atom, or a $(C_1-C_4)$alkyl group such as methyl or ethyl group;

z is an integer comprised inclusively between 0 and 50;

w is an integer comprised inclusively between 0 and 30;

with the proviso that (I) contains at least one carboxyl group C(O)OH, or C(O)O-$Q^+$ wherein $Q^+$ represents cation chosen from an alkali metal, an alkaline earth metal, or ammonium.

By polymerization of 1) and 2), it must be understood a copolymerization between at least one monomer 1) with at least one monomer 2).

According to an embodiment of the invention the copolymer comes from the polymerization between at least one ethylenically unsaturated mono or dicarboxylic acid monomer (1a) and at least one monomer which is an ester of formula (I) sas defined herein before or (2a):

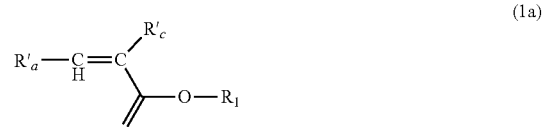

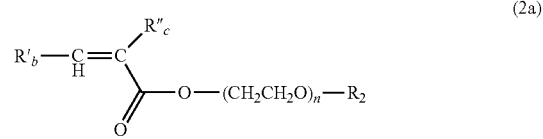

Formulas (1a) and (2a) wherein: $R'_a$ and $R'_b$, identical or different, represent a hydrogen atom, or a linear or branched $(C_1-C_6)$alkyl group, preferably $R'_a$ and $R'_b$ represent hydrogen atom; $R'_c$ and $R''_c$, identical or different, represent a hydrogen atom, or a linear or branched $(C_1-C_6)$alkyl group, a C(O)OX group, or a —alk-C(O)OX group wherein X represents a hydrogen atom, an alkali metal, alkaline earth metal, or ammonium and -alk- represents a $(C_1-C_6)$alkylene group such as methylene group, preferably $R'_c$ and/or $R''c$ represent a hydrogen atom or a methyl group;

$R_1$ represents a hydrogen atom, an alkali metal, alkaline earth metal, or a $(C_1-C_6)$alkyl group;

$R_2$ represents a, linear or branched, $(C_6-C_{40})$alkyl group, preferably a $(C_{10}-C_{30})$alkyl group;

n is an integer comprised inclusively between 5 and 100, particularly between 10 and 50, more particularly between 20 and 40, preferably between 20 and 30 such as 25;

with the proviso that (1a) or (2a) contain at least one carboxyl group C(O)OH, or C(O)O-$Q^+$ wherein $Q^+$ represents cation chosen from an alkali metal, alkaline earth metal or ammonium.

Particularly $R'_a$, $R'_b$ represent a hydrogen atom and $R'_c$, and $R''c$ represent a hydrogen atom or a methyl group and $R_1$ represents a hydrogen atom, an alkali metal, alkaline earth metal.

According to another variant $R'_a$, $R'_b$, and $R'c$, represent a hydrogen atom and $R''c$ represents a group -alk-C(O)OX such as —CH2-C(O)OX wherein X is as defined herein before.

According to a particular embodiment of the invention, the polymer i) contains units (Ia) and/or (I'a)

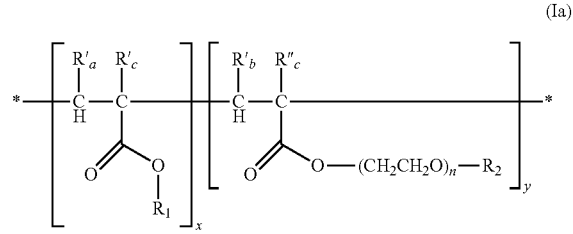

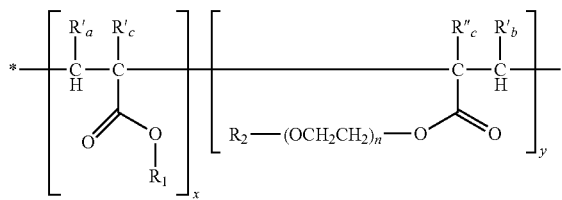

(I'a)

wherein $R'_a$, $R'_b$, $R'_c$, $R''c$ are as defined herein before;

x represents an integer, preferably more than 100, more preferably between 100 and 10000;

y represents an integer, preferably more than 100, more preferably between 100 and 10000;

and x+y represents an integer, preferably >200, more preferably between 200 and 20000.

According to a preferred embodiment, the anionic polymer i) of the present invention has a molecular weight of more than 100000, preferably between 200000 and 8000000.

According to a preferred embodiment, in formula (Ia) and (I'a), $R_1$ represents a hydrogen atom, an alkali metal, or an alkaline earth metal.

As example of copolymer (1a)/(2a) as defined herein before, usable in the invention, we may mention: acrylates/palmeth-25 acrylate copolymer, such as the products commercially available from 3V under the trade name Synthalen® W2000, acrylates/beheneth-25 methacrylate copolymer, such as the products commercially available from Lubrizol under the trade name Novethix® L-10, acrylates/steareth-20 methacrylate copolymer, such as the products commercially available from Rohm and Haas (Dow Chemical) under the trade name Aculyn™ 22 polymer, acrylates/steareth-20 itaconate copolymer, such as the products commercially available from AkzoNobel under the trade name Structure 2001, acrylates/ceteth-20 itaconate copolymer, such as the products commercially available from AkzoNobel under the trade name Structure 3001, acrylates/ceteth-20 methacrylate copolymer, acrylate/beheneth-25 itaconate copolymer, acrylate/palmeth-25 methacrylates copolymer, acrylate/steareth-50 acrylate copolymer, acrylates/palmeth-25 itaconate copolymer, such as the products commercially available from Sigma-3V under the trade name Polygel W 40, and mixtures thereof.

Among the above said polymers, the product sold by the company 3V Group under the tradename Synthalen® W2000 is specially preferred. This product is available in form of emulsions with 30% of the polymer. The anionic polymer described above are preferably used according to the invention in an amount which may range from 0.1% to 10% by weight, preferably from 0.5% to 8% by weight, more preferably from 1% to 5% by weight, relative to the total weight of the dye composition I.

Anionic Surfactant

The dye composition I according to the invention may further comprise one or more anionic surfactant(s).

The term "anionic surfactant" means a surfactant comprising, as ionic or ionizable groups, only anionic groups. These anionic groups are preferably chosen from the following groups:

—COOH, —COO⁻, —SO$_3$H, —SO$_3^-$, —OSO$_3$H, —OSO$_3^-$, —PO$_2$H$_2$, —PO$_2$H⁻, —PO$_2^{2-}$, —P(OH)$_2$, =P(O)OH, —P(OH)O⁻, =P(O)O—, —POH, =PO⁻, the anionic parts comprising a cationic counterion such as an alkali metal, an alkaline-earth metal or an ammonium.

As examples of anionic surfactants that may be used in the dye composition I according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids, and the corresponding non-salified forms of all these compounds; the alkyl and acyl groups of all these compounds comprising from 6 to 40 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycosidepolycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts, or alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts, and in particular sodium or magnesium salts, are preferably used.

Preferred anionic surfactants are chosen from ($C_6$-$C_{30}$) alkyl sulfates, ($C_6$-$C_{30}$)alkyl ether sulfates, ($C_6$-$C_{30}$)alkylamido ether sulfates, alkylaryl polyether sulfates and monoglyceride sulphates, all these compounds optionally comprising from 1 to 20 ethylene oxide units; and more preferably from ($C_{12}$-$C_{20}$)alkyl sulphates and ($C_{12}$-$C_{20}$)alkyl ether sulfates comprising from 2 to 20 ethylene oxide units, and even more preferably from 1 to 4 ethylene oxide units, especially in the form of alkali metal, ammonium, amino alcohol and alkaline-earth metal salts, or a mixture of these compounds. Better still, it is preferred to use a polyoxyethylenated sodium lauryl ether sulphate, such as sodium lauryl ether sulphate containing 2 or 2.2 mol of ethylene oxide.

Preferably, the anionic surfactants of the invention are sulfates, more specifically is chosen from ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates and monoglyceride sulfates, their salts such as alkali salts, such as sodium, and their mixtures.

More preferably the anionic surfactants of the invention are chosen from ($C_6$-$C_{30}$)alkyl sulfates, ($C_6$-$C_{30}$)alkyl ether sulfates, particularly ($C_6$-$C_{30}$)alkyl ether sulfates such as lauryl ether sulfate, their salts, such as sodium laureth sulfate.

The amount of said anionic surfactant(s) in the dye composition I according to the invention is 0.01 to 10% by weight, with regard to the total weight of the composition I.

Non-Ionic Surfactant

The dye composition I according to the invention may further contain one or more non-ionic surfactant(s).

The nonionic surfactant(s) that may be used in the compositions are described, for example, in the *Handbook of Surfactants* by M. R. Porter, published by Blackie & Son (Glasgow and London), 1991, pp. 116-178.

Examples of nonionic surfactants that may be mentioned include the following nonionic surfactants:

oxyalkylenated ($C_8$-$C_{24}$)alkylphenols;

saturated or unsaturated, linear or branched, oxyalkylenated or glycerolated $C_8$-$C_{40}$ alcohols, comprising one or two fatty chains;

saturated or unsaturated, linear or branched, oxyalkylenated $C_8$-$C_{30}$ fatty acid amides;

esters of saturated or unsaturated, linear or branched, $C_8$-$C_{30}$ acids and of polyethylene glycols;

esters of saturated or unsaturated, linear or branched, $C_8$-$C_{30}$ acids and of sorbitol, preferably oxyethylenated;

fatty acid esters of sucrose;

($C_8$-$C_{30}$)alkyl(poly)glucosides, ($C_8$-$C_{30}$)alkenyl(poly)glucosides, which are optionally oxyalkylenated (0 to 10 oxyalkylene units) and comprising from 1 to 15 glucose units, ($C_8$-$C_{30}$)alkyl (poly)glucoside esters;

saturated or unsaturated, oxyethylenated plant oils;

condensates of ethylene oxide and/or of propylene oxide, inter alia, alone or as mixtures;

N—($C_8$-$C_{30}$)alkylglucamine and N—($C_8$-$C_{30}$) acylmethylglucamine derivatives;

aldobionamides;

amine oxides;

oxyethylenated and/or oxypropylenated silicones;

and mixtures thereof.

The oxyalkylene units are more particularly oxyethylene or oxypropylene units, or a combination thereof, preferably oxyethylene units.

The number of moles of ethylene oxide and/or propylene oxide preferably ranges from 1 to 250, more particularly from 2 to 100 and better still from 2 to 50; the number of moles of glycerol ranges especially from 1 to 50 and better still from 1 to 10.

Advantageously, the nonionic surfactants according to the invention do not comprise any oxypropylene units.

As examples of glycerolated nonionic surfactants, use is preferably made of monoglycerolated or polyglycerolated $C_8$-$C_{40}$ alcohols, comprising from 1 to 50 mol of glycerol and preferably from 1 to 10 mol of glycerol.

As examples of compounds of this type, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleyl/cetyl alcohol containing 6 mol of glycerol, and octadecanol containing 6 mol of glycerol.

Among the glycerolated alcohols, it is more particularly preferred to use the $C_8$/$C_{10}$ alcohol containing 1 mol of glycerol, the $C_{10}$/$C_{12}$ alcohol containing 1 mol of glycerol and the $C_{12}$ alcohol containing 1.5 mol of glycerol.

The additional nonionic surfactant(s), when they are present in the dye composition I according to the invention, are preferably present in a total amount ranging from 0.01 to 1% by weight, with regard to the total weight of the composition.

Water

The dye composition I according to the invention advantageously comprises water, in a content of greater than or equal to 40% by weight relative to the total weight of composition.

The water content in the dye composition I according to the invention preferably ranges from 40% to 95% by weight, more preferentially from 50% to 90% by weight, or from 60% to 80% by weight, relative to the total weight of the composition I.

Organic Solvent

The dye composition I according to the invention may also comprise one or more water-soluble organic solvents (solubility of greater than or equal to 5% in water at 25° C. and at atmospheric pressure).

Examples of water-soluble organic solvents that may be mentioned include linear or branched and preferably saturated monoalcohols or diols, comprising 2 to 10 carbon atoms, such as ethyl alcohol, isopropyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as phenylethyl alcohol; polyols containing more than two hydroxyl functions, such as glycerol; polyol ethers, for instance ethylene glycol monomethyl, monoethyl and monobutyl ether, propylene glycol or ethers thereof, for instance propylene glycol monomethyl ether; and also diethylene glycol alkyl ethers, especially $C_1$-$C_4$ alkyl ethers, for instance diethylene glycol monoethyl ether or monobutyl ether, alone or as a mixture.

The water-soluble organic solvents, when they are present, generally represent between 1% and 20% by weight relative to the total weight of the dye composition I according to the invention, and preferably between 3% and 10% by weight, or between 4% and 8% by weight.

Alkaline Agent

The dye composition I according to the invention may further comprise one or more alkaline agents.

The alkaline agent(s) can especially be chosen from aqueous ammonia, alkali metal carbonates or bicarbonates, organic amines with a pKb at 25° C. of less than 12, in particular less than 10 and even more advantageously less than 6; from the salts of the amines mentioned previously with acids such as carbonic acid or hydrochloric acid: it should be noted that it is the pKb corresponding to the function of highest basicity.

Preferably, the composition I according to the present invention can be free of or substantially free of aqueous ammonia.

Preferably, the amines are chosen from alkanolamines, in particular comprising a primary, secondary or tertiary amine function, and one or more linear or branched $C_1$-$C_8$ alkyl groups bearing one or more hydroxyl radicals; from oxyethylenated and/or oxypropylenated ethylenediamines, and from amino acids and compounds having the following formula:

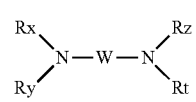

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

According to one embodiment of the invention, the dye composition I according to the invention comprises aqueous ammonia and/or at least one alkanolamine and/or at least one basic amino acid, more advantageously aqueous ammonia and/or at least one alkanolamine, such as monoethanolamine, or mixtures thereof.

Advantageously, the content of alkaline agent(s) ranges from 0.01% 30 to 30% by weight, preferably from 0.1% to 20% by weight, or from 1% to 10% by weight relative to the total weight of the composition I. It should be noted that this content is expressed as $NH_3$ when the alkaline agent is aqueous ammonia.

The pH of composition of the invention is preferably 8-11, preferably 8.5-10.5, and more preferably 9-10.

The pH can be adjusted by adding acidifying agents, such as hydrochloric acid, (ortho)phosphoric acid, sulfuric acid, boric acid, and also carboxylic acids, for instance acetic acid, lactic acid or citric acid, or sulfonic acids. Alkaline agents such as those previously mentioned may also be used.

Adjuvants

The dye composition I according to the invention may also comprise one or more cosmetic adjuvants.

For example, the composition I may comprise one or more additives that are well known in the art, such as anionic, nonionic or amphoteric polymers or mixtures thereof, agents for preventing hair loss, vitamins and provitamins including panthenol, such as vitamin A (retinol), vitamin E (tocopherol), vitamin C (ascorbic acid), vitamin B5 (panthenol), vitamin B3 (niacinamide), the derivatives of these vitamins (in particular esters) and their mixtures; sunscreens, mineral or organic pigments, sequestrants, plasticizers, solubilizers, acidifying agents, opacifiers, antioxidants, hydroxy acids, nacreous agents, fragrances and preserving agents.

Needless to say, a person skilled in the art will take care to select this or these optional additional compound(s) such that the advantageous properties intrinsically associated with the invention are not, or are not substantially, adversely affected by the envisaged addition(s).

The above adjuvants may generally be present in an amount, for each of them, of between 0 and 20% by weight, or between 0 and 10% by weight, relative to the total weight of the composition.

The composition I according to the invention may be in the form of fluid or thickened liquids, gels or creams.

The composition I advantageously has a viscosity, measured at ambient temperature and atmospheric pressure, ranging from 10 to 100 UD, preferably from 20 to 80 UD, and even more preferably from 35 to 70 UD, when using rotor 2 under 200 rpm for 30 seconds. The viscosity of the composition I of the present invention is measured using a ProRheo R180 machine from the company Prorheo, Roter 2 is used adapted to the viscosity of the composition to be tested (rotor is chosen for having a measure between 10 and 100 for UD Unit Deviation), the measure being made after 30 seconds rotating the rotor inside the composition, with a shear rate from $200\ s^{-1}$. The UD values may then be converted in Poises (1 Poise=0.1 Pa·s) with a correspondence table.

Oxidizing Composition II

The composition II of the dye kit according to the present invention comprises at least one oxidant.

Oxidant

The composition II of the present invention may comprise one or more oxidant. The term "oxidant" is intended to mean an oxidant other than atmospheric oxygen. More particularly, the oxidant is selected from the group consisting of hydrogen peroxide, urea peroxide, alkali metal bromates, peroxy salts, such as persulfates or perborates, peracids and their precursors, and alkali or alkaline earth metals; or a polymer type complex capable of releasing hydrogen peroxide.

Advantageously, the oxidizing agent is hydrogen peroxide.

The concentration of the oxidant may be from 0.1% by weight to 50% by weight, more preferably from 0.5% by weight to 20% by weight, still more preferably from 1% by weight to 15% by weight, based on the weight of the composition II.

Polysaccharide

The composition II of the present invention may comprise one or more polysaccharides.

In general, polysaccharides that are suitable for use in the present invention may be homopolysaccharides such as fructans, glucans, galactans and mannans or heteropolysaccharides such as hemicellulose.

Similarly, they may be linear polysaccharides such as pullulan or branched polysaccharides such as gum arabic and amylopectin, or mixed polysaccharides such as starch.

In general, the polysaccharides may be chosen from ones produced by microorganisms; polysaccharides isolated from algae, and higher plant polysaccharides, such as homogeneous polysaccharides, in particular celluloses and derivatives thereof or fructosans, heterogeneous polysaccharides such as gum arables, galactomannans, glucomannans, and derivatives thereof; and mixtures thereof.

In particular, the polysaccharides may be chosen from fructans, gellans, glucans, amylose, amylopectin, glycogen, pullulan, dextrans, celluloses and derivatives thereof, in particular methylcelluloses, hydroxyalkylcelluloses, ethylhydroxyethylcelluloses and carboxymethylcelluloses, mannans, xylans, lignins, arabans, galactans, galacturonans, chitin, chitosans, glucuronoxylans, arabinoxylans, xyloglucans, glucomannans, arabinogalactans, glycosaminoglucans, gum arables, tragacanth gums, ghatti gums, locust bean gums, galactomannans such as guar gums and nonionic derivatives thereof, in particular hydroxypropyl guar, and ionic derivatives thereof, biopoly saccharide gums of microbial origin, in particular scleroglucan or xanthan gums, mucopolysaccharides, and in particular chondroitin sulfates, and mixtures thereof. These polysaccharides may be chemically modified, especially with urea or urethane groups or by hydrolysis, oxidation, esterification, etherification, sulfatation, phosphatation, amination, amidation or alkylation reaction, or by several of these modifications.

The derivatives obtained may be anionic, cationic, amphoteric or nonionic.

Advantageously, the polysaccharides may be chosen from xanthan gum, scleroglucan gum, guar gum, inulin and pullulan, and mixtures thereof.

In general, the compounds of this type that may be used in the present invention are chosen from those described especially in Kirk-Othmer's Encyclopedia of Chemical Technology, Third Edition, 1982, volume 3, pp. 896-900, and volume 15, pp. 439-458, in Polymers in Nature by E. A. MacGregor and C. T. Greenwood, published by John Wiley & Sons, Chapter 6, pp. 240-328, 1980, in the book by Robert L. Davidson entitled Handbook of Water-Soluble Gums and Resins published by McGraw Hill Book Company (1980)

and in Industrial Gums—Polysaccharides and their Derivatives, edited by Roy L. Whistler, Second Edition, published by Academic Press Inc.

More precisely, these polysaccharides that are suitable for use in the present invention may be distinguished according to whether they are derived from microorganisms, from algae or from higher plants, and are detailed below.

Polysaccharides Produced by Microorganisms

Xanthan

Xanthan is a heteropolysaccharide produced at the industrial scale by the aerobic fermentation of the bacterium *Xanthomonas campestris*. Its structure consists of a main chain of β(1,4)-linked β-D-glucoses, similar to cellulose. One glucose molecule in two bears a trisaccharide side chain composed of an α-D-mannose, a β-D-glucuronic acid and a terminal β-D-mannose. The internal mannose residue is generally acetylated on carbon 6. About 30% of the terminal mannose residues bear a pyruvate group linked in chelated form between carbons 4 and 6. The charged pyruvic acids and glucuronic acids are ionizable, and are thus responsible for the anionic nature of xanthan (negative charge down to a pH equal to 1).

The content of pyruvate and acetate residues varies according to the bacterial strain, the fermentation process, the conditions after fermentation and the purification steps. These groups may be neutralized in commercial products with $Na^+$, $K^+$ or $Ca^{2+}$ ions (Satia company, 1986). The neutralized form may be converted into the acid form by ion exchange or by dialysis of an acidic solution.

Xanthan gums have a molecular weight of between 1,000,000 and 50,000,000 and a viscosity of between 0.6 and 1.65 Pa·s for an aqueous composition containing 1% of xanthan gum (measured at 25° C. on a Brookfield viscometer of LVT type at 60 rpm).

Xanthan gums are represented, for example, by the products sold under the names Rhodicare by the company Rhodia Chimie, under the name Satiaxane™ by the company Cargill Texturizing Solutions (for the food, cosmetic and pharmaceutical industries), under the name Novaxan™ by the company ADM, and under the names Kelzan® and Keltrol® by the company CP-Kelco.

Pullulan

Pullulan is a polysaccharide consisting of maltotriose units, known under the name α(1,4)-α(1,6)-glucan. Three glucose units in maltotriose are connected via an α(1,4) glycoside bond, whereas the consecutive maltotriose units are connected to each other via an α(1,6) glycoside bond.

Pullulan is produced, for example, under the reference Pullulan PF 20 by the group Hayashibara in Japan.

Dextran and Dextran Sulfate

Dextran is a neutral polysaccharide not bearing any charged groups, which is biologically inert, prepared by fermentation of beet sugar containing solely hydroxyl groups. It is possible to obtain dextran fractions of different molecular weights from native dextran by hydrolysis and purification. Dextran may in particular be in the form of dextran sulfate.

Dextran is represented, for example, by the products sold under the name Dextran or Dextran T by the company Pharmacosmos, or under the name Dextran 40 Powder or Dextran 70 Powder by the company Meito Sangyo Co. Dextran sulfate is sold by the company PK Chemical A/S under the name Dextran sulfate.

Succinoglycan

Succinoglycan is an extracellular polymer of high molecular weight produced by bacterial fermentation, consisting of octasaccharide repeating units (repetition of 8 sugars). Succinoglycans are sold, for example, under the name Rheozan by the company Rhodia. Scleroglucan Scleroglucan Scleroglucan is a nonionic branched homopolysaccharide consisting of β-D-glucan units. The molecules consist of a linear main chain formed from D-glucose units linked via β(1,3) bonds and of which one in three is linked to a side D-glucose unit via a β(1,6) bond.

A more complete description of scleroglucans and of their proion may be found in patent U.S. Pat. No. 3,301,848.

Scleroglucan is sold, for example, under the name Amigel by the company Alban Miller, or under the name Actigum™ CS by the company Cargill.

Polysaccharides Isolated from Algae

Furcellaran

Furcellaran is obtained commercially from red algae Furcellaria fasztigiata. Furcellaran is produced, for example, by the company Est-Agar.

Polysaccharides of Higher Plants

This category of polysaccharides may be divided into homogeneous polysaccharides (only one saccharide species) and heterogeneous polysaccharides composed of several types of saccharides.

a) Homogeneous polysaccharides and derivatives thereof

The polysaccharide according to the present invention may be chosen from celluloses and derivatives or fructosans.

Cellulose and Derivatives

The polysaccharide according to the present invention may also be a cellulose or a derivative thereof, especially cellulose ethers or esters (e.g. methylcellulose, carboxymethylcellulose, hydroxymethylcellulose, hydroxyethylcellulose, hydroxypropylcellulose, hydroxymethylpropylcellulose, cellulose acetate, cellulose nitrate, nitrocellulose).

The present invention may also contain a cellulose-based associative polymer.

According to the present invention, the term "cellulose-based compound" means any polysaccharide compound bearing in its structure linear sequences of anhydroglucopyranose residues (AGU) linked together via β(1,4) bonds. The repeating unit is the cellobiose dimer. The AGUs are in chair conformation and bear 3 hydroxyl functions: 2 secondary alcohols (in position 2 and 3) and a primary alcohol (in position 6). The polymers thus formed combine together via intermolecular bonds of hydrogen bond type, thus giving the cellulose a fibrillar structure (about 1500 molecules per fibre).

The degree of polymerization differs enormously depending on the origin of the cellulose; its value may range from a few hundred to several tens of thousands.

The hydroxyl groups of cellulose may react partially or totally with various chemical reagents to give cellulose derivatives having intrinsic properties. The cellulose derivatives may be anionic, cationic, amphoteric or nonionic. Among these derivatives, cellulose ethers, cellulose esters and cellulose ester ethers are distinguished.

Among the nonionic cellulose ethers, mention may be made of alkylcelluloses such as methylcelluloses and ethylcelluloses; hydroxyalkylcelluloses such as hydroxymethylcelluloses, hydroxyethylcelluloses and hydroxypropylcelluloses; and mixed hydroxyalkylalkylcelluloses such as hydroxypropylmethylcelluloses, hydroxy-ethylmethylcelluloses, hydroxy ethylethylcelluloses and hydroxybutylmethylcelluloses.

Among the anionic cellulose ethers, mention may be made of carboxyalkylcelluloses and salts thereof. By way of example, mention may be made of carboxymethylcelluloses, carboxymethylmethylcelluloses and carboxymethylhydroxy-ethylcelluloses and sodium salts thereof.

Among the cationic cellulose ethers, mention may be made of crosslinked or non-crosslinked, quaternized hydroxyethylcelluloses.

The quaternizing agent may in particular be glycidyltrimethylammonium chloride or a fatty amine such as laurylamine or stearylamine. Another cationic cellulose ether that may be mentioned is hydroxy ethylcellulosehydroxypropyltrimethylammonium.

The quaternized cellulose derivatives are, in particular:
quaternized celluloses modified with groups comprising at least one fatty chain, such as alkyl, arylalkyl or alkylaryl groups comprising at least 8 carbon atoms, or mixtures thereof,
quaternized hydroxyethylcelluloses modified with groups comprising at least one fatty chain, such as alkyl, arylalkyl or alkylaryl groups comprising at least 8 carbon atoms, or mixtures thereof.

The alkyl radicals borne by the above quaternized celluloses or hydroxyethylcelluloses preferably contain from 8 to 30 carbon atoms. The aryl radicals preferably denote phenyl, benzyl, naphthyl or anthryl groups.

Examples of quaternized alkylhydroxyethylcelluloses containing $C_{8-30}$ fatty chains that may be indicated include the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda.

Among the cellulose derivatives, mention may also be made of:
celluloses modified with groups comprising at least one fatty chain, for instance hydroxyethylcelluloses modified with groups comprising at least one fatty chain, such as alkyl groups, especially of $C_{8-22}$, arylalkyl and alkylaryl groups, such as Natrosol Plus Grade 330 CS ($C_{16}$ alkyls) sold by the company Aqualon, and
celluloses modified with polyalkylene glycol alkylphenyl ether groups, such as the product Amercell Polymer HM-1500 (nonylphenyl polyethylene glycol (15) ether) sold by the company Amerchol.

Among the cellulose esters are mineral esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.), and mixed organic/mineral esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

The cellulose-based compounds of the present invention may be chosen from unsubstituted celluloses and substituted celluloses. The celluloses and derivatives are represented, for example, by the products sold under the names Avicel® (microcrystalline cellulose, MCC) by the company FMC Biopolymers, under the name Cekol (carboxymethylcellulose) by the company Noviant (CP-Kelco), under the name Akucell AF (sodium carboxymethylcellulose) by the company Akzo Nobel, under the name Methocel™ (cellulose ethers) and Ethocel™ (ethylcellulose) by the company Dow, and under the names Aqualon® (carboxymethylcellulose and sodium carboxymethylcellulose), Benecel® (methylcellulose), Blanose™ (carboxymethylcellulose), Culminal® (methylcellulose, hydroxypropylmethylcellulose), Klucel® (hydroxypropylcellulose), PolysurfR (cetylhydroxyethylcellulose) and Natrosol® CS (hydroxy ethylcellulose) by the company Hercules Aqualon.

Fructosans

The polysaccharide according to the present invention may especially be a fructosan chosen from inulin and derivatives thereof (especially dicarboxy and carboxymethyl inulins).

Fructans or fructosans are oligosaccharides or polysaccharides comprising a sequence of anhydrofructose units optionally combined with several saccharide residues other than fructose. Fructans may be linear or branched. Fructans may be products obtained directly from a plant or microbial source or alternatively products whose chain length has been modified (increased or decreased) by fractionation, synthesis or hydrolysis, in particular enzymatic. Fructans generally have a degree of polymerization from 2 to about 1000 and preferably from 2 to about 60.

Three groups of fructans are distinguished. The first group corresponds to products whose fructose units are for the most part linked via β(2,1) bonds. These are essentially linear fructans such as inulins.

The second group also corresponds to linear fructoses, but the fructose units are essentially linked via β(2,6) bonds. These products are levans.

The third group corresponds to mixed fructans, i.e. containing β(2,6) and β(2,1) sequences. These are essentially branched fructans, such as graminans.

The preferred fructans in the compositions according to the present invention are inulins. Inulin may be obtained, for example, from chicory, dahlia or Jerusalem artichoke, preferably from chicory.

In particular, the polysaccharide, especially the inulin, has a degree of polymerization from 2 to about 1000 and preferably from 2 to about 60, and a degree of substitution of less than 2 on the basis of one fructose unit.

The inulin used for the present invention is represented, for example, by the products sold under the name Beneo™ inulin by the company Orafti, and under the name Frutafit® by the company Sensus.

b) Heterogeneous polysaccharides and derivatives thereof

The polysaccharides that may be used according to the present invention may be gums, for instance *cassia* gum, karaya gum, konjac gum, gum tragacanth, tara gum, acacia gum or gum arabic.

Gum Arabic

Gum arabic is a highly branched acidic polysaccharide which is in the form of mixtures of potassium, magnesium and calcium salts. The monomer elements of the free acid (arabic acid) are D-galactose, L-arabinose, L-rhamnose and D-glucuronic acid.

Galactomannans (guar, locust bean, fenugreek, tara gum) and derivatives (guar phosphate, hydroxypropyl guar, etc.)

Galactomannans are nonionic polyosides extracted from the endosperm of leguminous seeds, of which they constitute the storage carbohydrate.

Galactomannans are macromolecules consisting of a main chain of β(1,4)-linked D-mannopyranose units, bearing side branches consisting of a single D-galactopyranose unit α(1, 6)-linked to the main chain. The various galactomannans differ, firstly, by the proportion of α-D-galactopyranose units present in the polymer, and secondly, by significant differences in terms of distribution of galactose units along the mannose chain.

The mannose/galactose (M/G) ratio is about 2 for guar gum, 3 for tara gum and 4 for locust bean gum.

Guar

Guar gum is characterized by a mannose/galactose ratio of the order of 2/1. The galactose group is regularly distributed along the mannose chain.

The guar gums that may be used according to the present invention may be nonionic, cationic or anionic. According to the present invention, use may be made of chemically modified or unmodified nonionic guar gums.

The unmodified nonionic guar gums are, for example, the products sold under the names Vidogum GH, Vidogum G and Vidocrem by the company Unipektin and under the name Jaguar by the company Rhodia, under the name Meypro® Guar by the company Danisco, under the name Viscogum™ by the company Cargill, and under the name Supercol® guar gum by the company Aqualon.

The hydrolysed nonionic guar gums that may be used according to the present invention are represented, for example, by the products sold under the name Meyprodor® by the company Danisco.

The modified nonionic guar gums that may be used according to the present invention are preferably modified with $C_{1-6}$ hydroxyalkyl groups, among which mention may be made, for example, of hydroxymethyl, hydroxyethyl, hydroxypropyl and hydroxybutyl groups.

Such nonionic guar gums optionally modified with hydroxyalkyl groups are sold, for example, under the trade names Jaguar HP 60, Jaguar HP 105 and Jaguar HP 120 (hydroxypropyl guar) by the company Rhodia or under the name N-Hance® HP (hydroxypropyl guar) by the company Aqualon.

The cationic galactomannan gums preferably have a cationic charge density of less than or equal to 1.5 meq./g, more particularly between 0.1 and 1 meq./g. The charge density may be determined by the Kjeldahl method. It generally corresponds to a pH of the order of 3 to 9.

In general, for the purposes of the present invention, the term "cationic galactomannan gum" means any galactomannan gum containing cationic groups and/or groups that can be ionized into cationic groups.

The preferred cationic groups are chosen from those comprising primary, secondary, tertiary and/or quaternary amine groups.

The cationic galactomannan gums used generally have a weight-average molecular mass of between 500 and $5 \times 10^6$ approximately and preferably between 103 and $3 \times 10^6$ approximately.

The cationic galactomannan gums that may be used according to the present invention are, for example, gums comprising tri($C_{14}$)alkylammonium cationic groups. Preferably, 2% to 30% by number of the hydroxyl functions of these gums bear trialkylammonium cationic groups.

Among these trialkylammonium groups, mention may be made most particularly of trimethylammonium and triethylammonium groups.

Even more preferentially, these groups represent from 5% to 20% by weight relative to the total weight of the modified galactomannan gum.

According to the present invention, the cationic galactomannan gum is preferably a guar gum comprising hydroxypropyltrimethylammonium groups, i.e. a guar gum modified, for example, with 2,3-epoxypropyltrimethylammonium chloride.

These galactomannan gums, in particular guar gums modified with cationic groups are products already known per se and are, for example, described in patents U.S. Pat. Nos. 3,589,578 and 4,031,307. Such products are moreover sold especially under the trade names Jaguar EXCEL, Jaguar C13 S, Jaguar C 15, Jaguar C 17 and Jaguar CI 62 (Guar Hydroxypropyltrimonium Chloride) by the company Rhodia, under the name Amilan® Guar (Guar Hydroxypropyltrimonium Chloride) by the company Degussa, and under the name N-Hance® 3000 (Guar Hydroxypropyltrimonium Chloride) by the company Aqualon.

The anionic guar gums that may be used according to the present invention are polymers comprising groups derived from carboxylic, sulfonic, sulfenic, phosphoric, phosphonic or pyruvic acid. The anionic group is preferably a carboxylic acid group. The anionic group may also be in the form of an acid salt, especially a sodium, calcium, lithium or potassium salt.

The anionic guar gums that may be used according to the present invention are preferentially carboxymethyl guar derivatives (carboxymethyl guar or carboxymethyl hydroxypropyl guar).

Locust Bean

Locust bean gum is extracted from the seeds of the locust bean tree *Ceratonia siliqua*).

The unmodified locust bean gum that may be used in the present invention is sold, for example, under the name Viscogum™ by the company Cargill, under the name Vidogum L by the company Unipektin and under the name Grinsted® LBG by the company Danisco.

The chemically modified locust bean gums that may be used in the present invention may be represented, for example, by the cationic locust beans sold under the name Catinal CLB (locust bean hydroxypropyltrimonium chloride) by the company Toho.

Tara Gum

The tara gum that may be used in the context of the present invention is sold, for example, under the name Vidogum SP by the company Unipektin.

Glucomannans (Konjac Gum)

Glucomannan is a polysaccharide of high molecular weight (500,000<Mglucomannan<2,000,000) composed of D-mannose and D-glucose units with a branch every 50 or 60 units approximately. It is found in wood, but is also the main constituent of konjac gum. Konjac (Amorphophallus konjac) is a plant of the Araceae family.

The products that may be used according to the present invention are sold, for example, under the names Propol® and Rheolex® by the company Shimizu.

Other Polysaccharides

Among the other polysaccharides that may be used according to the present invention, mention may also be made of chitin (poly-N-acetyl-D-glucosamine, β(1,4)-2-acetamido-2-deoxy-D-glucose), chitosan and derivatives (chitosan-β-glycerophosphate, carboxymethylchitin, etc.) such as those sold by the company France-Chitine; glycosaminoglycans (GAG) such as hyaluronic acid, chondroitin sulfate, dermatan sulfate, keratan sulfate, and preferably hyaluronic acid; xylans (or arabinoxylans) and derivatives.

Arabinoxylans are polymers of xylose and arabinose, all grouped under the name pentosans. Xylans consist of a main chain of β(1,4)-linked D-xylose units and on which are found three substituents (Rouau & Thibault, 1987): acid units, α-L-arabinofuranose units, side chains which may contain arabinose, xylose, galactose and glucuronic acid.

According to this variant, the polysaccharide is preferably xanthan gum.

The polysaccharide may be present in an amount ranging for example from 0.001 to 10% by weight, preferably 0.01 to 5% by weight and more preferably from 0.04 to 3% by weight relative to the total weight of the composition II.

Chelating Agent

The composition II of the present invention may comprise at least one chelating agent.

According to the present invention, the useful chelating agent comprises aminocarboxylic acids, e.g., elhylenediamine tetraacetic acid (EDTA), aminotriacetic acid, diethylene triaminepentaacetic acid, and in particular the alkali metal salt thereof, e.g., N,N-bis(carboxymethyl)glutamic acid, tetrasodium EDTA, tetrasodium salt of N,N-bis(carboxymethyl)glutamic acid (glutamic acid diacetic acid, GLDA); hydroxyl carboxylic acids, e.g., citric acid, tartaric acid, glucuronic acid, succinic acid, ethylenediamine disuccinic acid (EDDS), and in particular the alkali metal salt thereof; hydroxyl aminocarboxylic acids, e.g., hydroxyethylethylenediamine triacetic acid (HEDTA), dihydroxyethylglycine (DEG), and in particular the alkali metal salt thereof; polyphosphonic acid, and in particular the alkali metal salt thereof; other phosphor-containing organic acid, e.g., phytic acid, and in particular the alkali metal salt thereof, e.g., sodium phytate, potassium phytate polycarboxylic acid, e.g., polyacrylic acid, polymethacrylic acid, and in particular the alkali metal salt thereof.

In one embodiment, the at least one water soluble chelating agent is an alkali metal hydroxyl polycarboxylate represented by an alkane containing from 1 to 4 carbon atoms, preferably containing 2 or 3 carbon atoms, substituted by 1, 2, or 3 hydroxyl groups (—OH), preferably by one (1) hydroxyl group, and further substituted by 2, 3, 4 or 5 carboxylate groups (—COOM), preferably by 2 or 3 carboxylate groups (—COOM), wherein the multiple groups M independently represent H or alkali metal, with the proviso that at least one of the groups M represents alkali metal, such as Na, K or Li, preferably all groups M represent alkali metal, such as Na, K or Li, preferably Na. More specifically, the at least one alkali metal hydroxyl polycarboxylate may be chosen from sodium tartrates, sodium citrates, potassium tartrates, potassium citrates, and hydrates thereof, preferably sodium citrates, in particularly trisodium citrate. Herein, sodium citrates are used to indicate monosodium citrate, disodium citrate and trisodium citrate, and other alkali metal hydroxyl polycarboxylates may be understood in a similar way.

Amongst others, the alkali metal mentioned above is preferably sodium or potassium, in particular sodium. Accordingly, preferable chelating agents can comprise sodium citrate, tetrasodium EDTA, tetrasodium GLDA, trisodium EDDS, sodium phytate, or a mixture thereof.

In particular, the composition II of the present invention may comprise the at least one water soluble chelating agent in a content ranging from 0.01% to 1% by weight, especially from 0.1% to 0.4% by weight, relative to the total weight of the second composition.

AMPS Polymers

The composition II of the present invention may also comprise at least one AMPS polymer.

The AMPS polymers used in accordance with the invention are crosslinked or non-crosslinked homopolymers or copolymers comprising at least the acrylamido-2-methylpropanesulfonic acid monomer, in a form partially or totally neutralized with a mineral base other than ammonia, such as sodium hydroxide or potassium hydroxide.

They are preferably totally neutralized or virtually totally neutralized, i.e. at least 90% neutralized.

These AMPS polymers according to the invention may be crosslinked or non-crosslinked.

When the polymers are crosslinked, the crosslinking agents may be chosen from the polyolefinically unsaturated compounds commonly used for the crosslinking of polymers obtained by free-radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allylic or vinyl ethers of polyfunctional alcohols, and also allylic esters of phosphoric and/or vinylphosphonic acid derivatives, or mixtures of these compounds.

According to one embodiment of the invention, the crosslinking agent is chosen from methylenebis-acrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The AMPS polymers in accordance with the invention are preferably water-soluble or water-dispersible. In this case they are:
either "homopolymers" comprising only AMPS monomers and, if they are crosslinked, one or more crosslinking agents such as those defined above;
or copolymers obtained from AMPS and from one or more hydrophilic or hydrophobic ethylenically unsaturated monomers and, if they are crosslinked, one or more crosslinking agents such as those defined above. When the said copolymers comprise hydrophobic ethylenically unsaturated monomers, these monomers do not comprise a fatty chain and are preferably present in small amounts.

For the purposes of the AMPS polymer according to the present invention, the term "fatty chain" means any hydrocarbon-based chain containing at least 7 carbon atoms.

The term "water-soluble or water-dispersible" means polymers which, when introduced into an aqueous phase at 25° C., to a mass concentration equal to 1%, make it possible to obtain a macroscopically homogeneous and transparent solution, i.e. a solution that has a maximum light transmittance value, at a wavelength equal to 500 nm, through a sample 1 cm thick, of at least 60% and preferably of at least 70%.

The "homopolymers" according to the invention are preferably crosslinked and neutralized.

The AMPS homopolymers according to the invention are preferably optionally crosslinked and/or neutralized 2-acrylamido-2-methylpropanesulfonic acid homopolymers, for instance the poly(2-acrylamido-2-methylpropanesulfonic acid) sold by the company Clariant under the name Hostacerin AMPS® (CTFA name: ammonium polyacryldimethyltauramide).

The water-soluble or water-dispersible AMPS copolymers according to the invention contain water-soluble ethylenically unsaturated monomers, hydrophobic monomers or mixtures thereof.

The water-soluble comonomers may be ionic or nonionic.

Among the ionic water-soluble comonomers, examples that may be mentioned include the following compounds and the salts thereof:
(meth)acrylic acid,
styrenesulfonic acid,
vinylsulfonic acid and (meth)allylsulfonic acid,
vinylphosphonic acid,
maleic acid,
itaconic acid,
crotonic acid, the water-soluble vinyl monomers of formula (A) below:

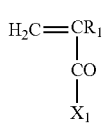

in which:
R$_1$ is chosen from H, —CH$_3$, —C$_2$H$_5$ and —C$_3$H$_7$
X$_1$ is chosen from:
alkyl ethers of —OR$_2$ type in which R$_2$ is a linear or branched, saturated or unsaturated hydrocarbon-based radical containing from 1 to 6 carbon atoms, substituted with at least one sulfonic (—SO$_3$—) and/or sulfate (—SO$_4$—) and/or phosphate (—P04H$_2$—) group.

Among the nonionic water-soluble comonomers, examples that may be mentioned include:
(meth)acrylamide,
N-vinylacetamide and N-methyl-N-vinylacetamide,
N-vinylformamide and N-methyl-N-vinylformamide,
maleic anhydride,
vinylamine,
N-vinyllactams comprising a cyclic alkyl group containing 4 to 9 carbon atoms, such as n-vinylpyrrolidone, N-butyrolactam and N-vinylcaprolactam,
vinyl alcohol of formula CH$_2$=CHOH,
the water-soluble vinyl monomers of formula (B) below:

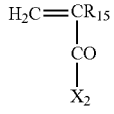

in which:
R$_{15}$ is chosen from H, —CH$_3$, —C$_2$H$_5$ and —C$_3$H$_7$
X$_2$ is chosen from:
alkyl ethers of —OR$_{16}$ type in which R$_{16}$ is a linear or branched, saturated or unsaturated hydrocarbon-based radical containing from 1 to 6 carbons, optionally substituted with a halogen atom (iodine, bromine, chlorine or fluorine); a hydroxyl group (—OH); ether.

Mention is made, for example, of glycidyl (meth)acrylate, hydroxyethyl methacrylate and (meth)acrylates of ethylene glycol, of diethylene glycol or of polyalkylene glycol.

Among the fatty-chain-free hydrophobic comonomers, examples that may be mentioned include:
styrene and its derivatives, such as 4-butylstyrene, α-methylstyrene and vinyltoluene,
vinyl acetate of formula CH$_2$=CH—OCOCH$_3$;
vinyl ethers of formula CH$_2$=CHOR in which R is a linear or branched, saturated or unsaturated hydrocarbon-based radical containing from 1 to 6 carbons;
acrylonitrile,
caprolactone,
vinyl chloride and vinylidene chloride,
silicone derivatives, which lead to silicone polymers after polymerization, such as methacryloxypropyltris(trimethylsiloxy)silane and silicone methacrylamides, the hydrophobic vinyl monomers of formula (C) below:

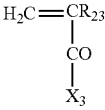

in which:
R$_{23}$ is chosen from H, —CH$_3$, —C$_2$H$_5$ and —C$_3$H$_7$
X$_3$ is chosen from:
alkyl ethers of —OR$_{24}$ type in which R$_{24}$ is a linear or branched, saturated or unsaturated hydrocarbon-based radical containing from 1 to 6 carbon atoms.

Mention is made, for example, of methyl methacrylate, ethyl methacrylate, n-butyl (meth)acrylate, tert-butyl (meth)acrylate, cyclohexyl acrylate and isobornyl acrylate and 2-ethylhexyl acrylate.

The AMPS polymers, preferably water-soluble or water-dispersible, of the invention preferably have a molar mass ranging from 50 000 g/mol to 10,000,000 g/mol, preferably from 80 000 g/mol to 8,000,000 g/mol and even more preferably from 100 000 g/mol to 7,000,000 g/mol.

Examples of water-soluble or water-dispersible AMPS homopolymers in accordance with the invention that may be mentioned include crosslinked or non-crosslinked polymers of sodium acrylamido-2-methylpropanesulfonate, such as the polymer used in the commercial product Simulgel 800 (CTFA name: Sodium Polyacryloyldimethyltaurate).

Examples of water-soluble or water-dispersible AMPS copolymers in accordance with the invention that may be mentioned include:
acrylamide/sodium acrylamido-2-methylpropanesulfonate crosslinked copolymers, such as the copolymer used in the commercial product Sepigel 305 (CTFA name: Polyacrylamide/C$_{13}$-C$_{14}$ Isoparaffin/Laureth-7) or the copolymer used in the commercial product sold under the trade name Simulgel 600 (CTFA name: Acrylamide/Sodium Acryloyldimethyltaurate/Isohexadecane/Polysorbate-80) by the company SEPPIC;
copolymers of AMPS and of vinylpyrrolidone or of vinylformamide, such as the copolymer used in the commercial product sold under the name Aristoflex AVC by the company Clariant (CTFA name: Ammonium Acryloyldimethyltaurate/VP Copolymer) but neutralized with sodium hydroxide or potassium hydroxide;
copolymers of AMPS and of sodium acrylate, for instance AMPS/sodium acrylate copolymer such as the copolymer used in the commercial product sold under the name Simulgel EG by the company SEPPIC (CTFA name: Acrylamide/Sodium Acryloyldimethyltaurate/Isohexadecane/Polysorbate-80);
copolymers of AMPS and of hydroxyethyl acrylate, for instance AMPS/hydroxyethyl acrylate copolymer, such as the copolymer used in the commercial product sold under the name Simulgel NS by the company SEPPIC (CTFA name: Hydroxyethyl acrylate/Sodium Acryloyldimethyltaurate copolymer (and) Squalane (and) Polysorbate-60);
ammonium acryloyldimethyltaurate/steareth-25 methacrylate crosspolymer.

The preferred polymers are more particularly sodium acrylamido-2-methylpropanesulfonate homopolymers, such as the homopolymer used in the commercial product Sepigel 800, and AMPS/hydroxyethyl acrylate copolymers, such as the copolymer used in the commercial product sold under the name Simulgel NS, or ammonium acryloyldimethyltaurate/steareth-25 methacrylate crosspolymer.

The AMPS polymers in accordance with the invention are generally present in amounts ranging from 0.01% to 10% by weight, more preferably from even more preferably from 0.1% to 5% by weight and even more particularly from 0.3% to 1% by weight relative to the total weight of the composition II.

The compositions according to the invention may be in the form of fluid or thickened liquids, gels or creams.

They advantageously have a viscosity, measured at ambient temperature and atmospheric pressure, ranging from 10 to 100 UD, preferably from 20 to 80 UD, and even more preferably from 35 to 70 UD, when using rotor 2 under 200 rpm for 30 seconds. The viscosity of the composition of the present invention is measured using a ProRheo R180 machine from the company Prorheo, Roter 2 is used adapted to the viscosity of the composition to be tested (rotor is chosen for having a measure between 10 and 100 for UD Unit Deviation), the measure being made after 30 seconds rotating the rotor inside the composition, with a shear rate from 200 s$^{-1}$. The UD values may then be converted in Poises (1 Poise=0.1 Pa·s) with a correspondence table.

Use

The invention also relates to the use of the dye kit as described above for dyeing keratin fibres, in particular the hair.

Another subject of the invention is a process for dyeing human keratin fibres, in particular the hair, using the dye kit as described above.

According to a preferred embodiment, the dyeing process of the invention comprises mixing the dye composition I and the composition II immediately before use, and applying the mixture obtained as described above to the keratin fibres.

More particularly, by "mixing" or a variant thereof, it is intended to mean the action of putting the dye composition I of the present invention into a container or palm, together with the oxidizing composition II as described above, with or without stirring them.

According to a preferred variant of the preferred embodiment, the dye composition I of the present invention is put into a container or palm together with the oxidizing composition II as described above, without stirring them.

Irrespective of the process used and the number of compositions used, the composition(s) described previously, optionally mixed beforehand, are applied to wet or dry keratin fibres.

The composition(s) are usually left in place on the fibres for a time generally ranging from 1 minute to 1 hour and preferably from 5 minutes to 30 minutes.

The temperature during the process is conventionally between 20 and 80° C. and preferably between 20 and 60° C. After the treatment, the human keratin fibres are advantageously rinsed with water. They may optionally be further washed with a shampoo, followed by rinsing with water, before being dried or left to dry.

The process may be repeated several times in order to obtain the desired coloration.

Another subject of the invention concerns a multi-compartment device, comprising at least two compartments:
- a first compartment containing a dye composition I as described above; and
- a second compartment containing an oxidizing composition II as described above.

According to one variant of the invention, an additional compartment containing an additional composition comprising one or more treating agents is provided.

The compositions of the kit are packaged in separate compartments, which may be optionally accompanied by suitable identical or different application means, such as fine brushes, coarse brushes or sponges.

The abovementioned dye kit may also be equipped with means allowing the delivery to the hair of the desired mixture, such as, for example, the device described in patent FR 2 586 913.

The examples that follow are given purely as illustrations of the present invention.

EXAMPLES

The ingredient amounts/concentrations in the compositions/formulas described below are expressed in % by weight, relative to the total weight of each composition/formula.

Example 1

The dye compositions I hereunder were prepared, from the ingredients indicated in the table below (in which the contents are indicated in grams of active material with regard to the total weight of the composition):

Comparative compositions C/F/G/D/E, and inventive compositions H/M were formulated according to Table 1 below:

TABLE 1

| Ingredients | C | F | G | D | E | H | M |
|---|---|---|---|---|---|---|---|
| p-PHENYLENEDIAMINE | 2 | 2 | 2 | 2 | 2 | 2 | 2 |
| RESORCINOL | 1.7 | 1.7 | 1.7 | 1.7 | 1.7 | 1.7 | 2 |
| N,N-BIS(2-HYDROXYETHYL)-p-PHENYLENEDIAMINE SULFATE | 0.3 | 0.3 | 0.3 | 0.3 | 0.3 | 0.3 | 0.4 |
| m-AMINOPHENOL | 0.25 | 0.25 | 0.25 | 0.25 | 0.25 | 0.25 | 0.3 |
| 2,4-DIAMINOPHENOXYEHANOL T HCL | 0.8 | 0.8 | 0.8 | 0.8 | 0.8 | 0.8 | 1 |
| TOLUENE-2,5-DIAMINE | | | | | | | 0.7 |
| ASCORBIC ACID | 0.3 | 0.5 | 0.5 | 0.5 | 0 | 0 | 0.3 |
| SODIUM METABISULFITE | 0.7 | 0.7 | 1 | 1.3 | 0 | 0 | 0.7 |
| SODIUM SULFITE | 0 | 0 | 0 | 0 | 0.5 | 0 | 0 |
| ERYTHORBIC ACID | 0 | 0 | 0 | 0 | 0.5 | 0 | 0 |
| THIOGLYCOLIC ACID | 0 | 0 | 0 | 0 | 0 | 0.4 | 0 |
| ETHANOLAMINE THIOGLYCOLATE | 0 | 0 | 0 | 0 | 0 | 0 | 0.6 |

TABLE 1-continued

| Ingredients | C | F | G | D | E | H | M |
|---|---|---|---|---|---|---|---|
| ETHANOLAMINE | 4.0 | 4.0 | 4.0 | 4.0 | 4.0 | 1.6 | 4.0 |
| HYDROXYBENZOMORPHOLINE | 0.4 | 0.4 | 0.4 | 0.4 | 0.4 | 0.4 | 0.7 |
| ACRYLATES/PALMETH-25 ACRYLATE COPOLYMER | 1.2 | 1.2 | 1.2 | 1.2 | 1.2 | 1.2 | 1.2 |
| GLYCERIN | 5 | 5 | 5 | 5 | 5 | 5 | 5 |
| EDTA | 0.15 | 0.15 | 0.15 | 0.15 | 0.15 | 0.15 | 0.15 |
| WATER | QS 100 g | QS 100 g | QS 100 g | QS 100 g | QS 100 g | QS 100 g | QS 100 g |

The compositions above were tested with regard to the following properties:

Compatibility test in plastic packaging was conducted at 50 C for 2 weeks, room temperature (25° C.) for 2 weeks and in aluminum tubes for reference. Oxidation level is directly linked to the texture color, so pictures were taken in light box to compare the oxidation level. Yellower or darker means higher oxidation level and poorer compatibility with plastic packaging.

Viscosity of the composition: The viscosities of the compositions C, F, G, D, E, H, and M were measured at 25° C., using a ProRheo R180 machine from the company Prorheo, Roter 2 was used adapted to the viscosity of the product to be tested (rotor is chosen for having a measure between 10 and 100 for UD Unit Deviation), the measure being made after 30 seconds rotating the rotor inside the composition, with a shear rate from 200 s$^{-1}$. The UD values may then be converted in Poises (1 Poise=0.1 Pa·s) with a correspondence table. For application, the ease of application onto hair of the compositions C, F, G, D, E, H, and M were respectively measured by 3 hair dressers using the compositions C, F, G, D, E, H, and M for dyeing the hair. 20 g of the compositions C, F, G, D, E, H, and M were each poured in the palm of the hair dressers, respectively, together with 30 g amount of an oxidizer containing 6% of hydrogen peroxide. After mixing, the hair dressers applied the products (compositions C, F, G, D, E, H, M mixing with oxidizers) immediately onto the middle-length hair, i.e., hair length was at the shoulder. The hair was massaged and foam was formed. After 15 minutes, the hair with the products mentioned above was rinsed with water.

For each property, a score was attributed to each composition on a scale ranging from 1 to 5 as follows 1: very bad
2: not good
3: acceptable
4: good
5 perfect Results were showed in Table 2.

The results hereabove clearly showed that the particular combination of surfactants of the dye composition I according to the invention allowed achieving superior performances in terms of working compatibility with plastic packaging and application.

Example 2

A dye composition in accordance with the invention was prepared, from the ingredients indicated in the table 3 below (in which the contents are indicated in grams of active material with regard to the total weight of the composition):

TABLE 3

| Ingredients | P9 |
|---|---|
| FRAGRANCE | 0.7 |
| p-PHENYLENEDIAMINE | 2.5 |
| RESORCINOL | 2 |
| ETHANOLAMINE THIOGLYCOLATE | 0.7 |
| ETHANOLAMINE | 3.5 |
| HYDROXYBENZOMORPHOLINE | 0.7 |
| SODIUM LAURETH SULFATE | 2.1 |
| ASCORBIC ACID | 0.25 |
| N,N-BIS(2-HYDROXYETHYL)-p-PHENYLENEDIAMINE SULFATE | 0.4 |
| GLYCERIN | 5 |
| m-AMINOPHENOL | 0.3 |
| EDTA | 0.15 |
| 2,4-DIAMINOPHENOXYETHANOL HCL | 1.1 |
| SODIUM METABISULFITE | 0.7 |
| CARBOMER | 0.9 |
| ACRYLATES/BEHENETH-25 METHACRYLATE COPOLYMER | 0.3 |
| WATER | QS to 100 |

20 g of the dye composition prepared above and 30 g of an oxidizing composition containing 600 of hydrogen peroxide were kept in a plastic device which could packaging two compositions separately during transportation and stor-

TABLE 2

| Properties | C | F | G | D | E | H | M |
|---|---|---|---|---|---|---|---|
| Texture color | Very dark yellow | Dark yellow | Dark yellow | Medium dark yellow | Medium dark yellow | Slightly yellow | Slightly yellow |
| Compatibility with plastic packaging | 1 | 2 | 2 | 2 | 2 | 4 | 5 |
| Viscosity | 5 | 5 | 5 | 5 | 5 | 5 | 5 |
| Application | 3 | 3 | 3 | 4 | 4 | 5 | 5 | age. The two compositions were mixed on first use thanks to the function of the device. After mixing, the compositions were applied immediately onto the middle-length hair, i.e., hair length was at the shoulder. The hair was massaged and foam was formed. After 15 minutes, the hair was rinsed with water.

The viscosity of the composition mentioned above was 38 UD, using the measurement method disclosed in example 1 above. It allowed the composition staying in the palm without floating away. And furthermore, when mixing with the oxidizer on the hair, it allowed the mixture and the foam staying on the hair without dropping or flying.

It was a clear and transparent composition, which was very pleasant to the consumers.

The composition mentioned above was stable over 2 months under 4° C., room temperature, and 45° C.

Inventors observed that without waiting for a long period of time, the hair was dyed as expected. Within 15 minutes staying on the hair, the gray hair was covered perfectly.

The invention claimed is:

1. A dye composition, comprising:
   (a) an oxidative dye;
   (b) a thickener comprising an anionic polymer; and
   (c) an antioxidant comprising a thiol-dertved reducer.

2. The dye composition of claim 1, wherein the oxidative dye comprises an oxidation base comprising a para-phenylenediamine, bis(phenyl)alkylenediamine, para-aminophenol, ortho-aminophenol, and/or heterocyclic base, optionally in addition salt form.

3. The composition of claim 1, wherein the oxidative dye further comprises a coupler comprising a meta-phenylenediamine, meta-aminophenol, meta-diphenol, naphthalene-based coupler, and/or heterocyclic coupler, optionally in addition salt form.

4. The composition of claim 1, wherein the anionic polymer is obtained by a process comprising copolymerizing components (1) and (2) comprising:
   (1) an ethylenically unsaturated mono or dicarboxylic acid monomer substituted by at least one, linear or branched, $(C_1-C_{10})$alkyl group; and
   (2) an ester monomer of formula (I):

$$A\text{-}O\text{-}(Alk\text{-}O)_z\text{-}(CH_2)_w\text{-}R^a \quad (I)$$

wherein
A is an ethylenically unsaturated acyclic residue, optionally comprising an additional carboxylic group, optionally as a salt or esterified with a linear or branched $(C_1-C_{20})$alkyl group,
$R^a$ is a $(C_1-C_{30})$alkyl group, $(C_1-C_{30})$alkylaryl, or $(C_1-C_{30})$arylalkyl group, the alkyl group being linear or branched,
Alk a linear or branched $(C_1-C_6)$alkylene group,
z is an integer in a range of from 0 to 50, and
w is an integer in a range of from 0 to 30,
with the proviso that formula (I) comprises a carboxyl group C(O)OH, or C(O)O-$Q^+$, $Q^+$ being an alkali metal, an alkaline earth metal, or ammonium.

5. The composition of claim 1, wherein the thiol-derived reducer comprises thioglycolic acid, dithioglycolic acid, thiolactic acid, and/or thiomalic acid, optionally in salt form.

6. The composition of claim 1, wherein antioxidant further comprises a natural exogenous phytochemical antioxidant, flavonoid, vitamin, a vitamin derivative, tocopherol, tocotrienol phenol, carotenoid, anthocyanin, dihydrochalcone, phenylpropanoid, chalcone, curcuminoid, tannin, stilbenoid, coumarin, and/or carotenoid.

7. The composition of claim 1, wherein the antioxidant is present in a range of from 0.001 to 5 wt. % relative to total dye composition weight.

8. A kit, comprising:
   (1) the dye composition of claim 1; and
   (2) an oxidizing composition comprising d) an oxidant.

9. The kit of claim 8, wherein the oxidant comprises hydrogen peroxide, urea peroxide, an alkali metal bromate, peroxy salt, and/or a polymer type complex capable of releasing hydrogen peroxide.

10. The kit of claim 8, wherein the concentration of the oxidant is in a range of from 0.1 to 50 wt. %, based on total oxidizine composition weight.

11. A multi compartment package, comprising:
    the kit of claim 8;
    a first compartment comprising the dye composition; and
    a second compartment comprising the oxidizing composition,
    wherein the dye composition and the oxidizing composition are placed in different compartments separate from one another.

12. The package of claim 11, wherein the compartments are made of plastic.

13. A process of improving compatibility of an oxidizing substance with plastic, the process comprising:
    mixing a thiol-derived reducer with the oxidizing substance.

14. The process of claim 13, wherein the thiol-derived reducer comprises thioglycolic acid, dithio glycolic acid, thiolactic acid, and/or thiomalic acid, optionally in salt form.

15. The composition of claim 1, wherein the anionic polymer comprises an acrylate/palmeth-25-acrylate copolymer, acrylate/beheneth-25-methacrylate copolymer, acrylate/steareth-20-methacrylate copolymer, acrylate/steareth-20-itaconate copolymer, acrylate/ceteth-20-itaconate copolymer, acrylate/ceteth-20-methacrylate copolymer, acrylate/beheneth-25-itaconate copolymer, acrylate/palmeth-25-methacrylate-copolymer, acrylate/steareth-50-acrylate copolymer, and/or acrylate/palmeth-25-itaconate copolymer.

16. The composition of claim 1, wherein the thiol-derived reducer comprises thioglycolic acid, optionally in salt form.

17. The composition of claim 1. wherein the thiol-derived reducer comprises dithioglycohc acid, optionally in salt form.

18. The composition of claim 1, wherein the thiol-derived reducer comprises thiolactic acid, optionally in salt form.

19. The composition of claim 1, wherein the thiol-derived reducer comprises thiomalic acid, optionally in salt form.

20. The composition of claim 1, wherein the antioxidant is present in a. range of from 0.35 to 2 wt % relative to total dye composition weight.

* * * * *

UNITED STATES PATENT AND TRADEMARK OFFICE
CERTIFICATE OF CORRECTION

PATENT NO. : 11,752,082 B2
APPLICATION NO. : 17/623074
DATED : September 12, 2023
INVENTOR(S) : Huang et al.

It is certified that error appears in the above-identified patent and that said Letters Patent is hereby corrected as shown below:

On the Title Page

Item (57), under "ABSTRACT", Line 5, delete "IL," and insert -- II, --, therefor.

In the Claims

In Column 31, Claim 1, Line 24, delete "thiol-dertved" and insert -- thiol-derived --, therefor.

In Column 31, Claim 4, Line 51, after "Alk", insert -- a --.

In Column 32, Claim 6, Line 1, after "wherein", insert -- the --.

In Column 32, Claim 11, Line 20, delete "multi compartment" and insert -- multi-compartment --, therefor.

In Column 32, Claim 17, Line 50, delete "dithioglycohc" and insert -- dithioglycolic --, therefor.

Signed and Sealed this
Twelfth Day of December, 2023

Katherine Kelly Vidal
Director of the United States Patent and Trademark Office